United States Patent
Van Driel

[19]

[11] Patent Number: 5,951,508
[45] Date of Patent: Sep. 14, 1999

[54] BILATERALLY CONNECTABLE SOFTSHELL RESERVOIR

[75] Inventor: Michael R. Van Driel, Fountain Valley, Calif.

[73] Assignee: Medtronic, Inc., Minneapolis, Minn.

[21] Appl. No.: 08/939,382

[22] Filed: Sep. 29, 1997

[51] Int. Cl.$^6$ .............................. A61M 37/00; A61M 1/14
[52] U.S. Cl. ................ 604/4; 422/310; 604/533
[58] Field of Search .................... 422/310; 604/4, 604/408, 533

[56] References Cited

U.S. PATENT DOCUMENTS

| | | | |
|---|---|---|---|
| 4,602,910 | 7/1987 | Larkin | 604/87 |
| 4,734,269 | 3/1988 | Clarke et al. | 422/310 |
| 4,795,457 | 1/1989 | Cooney | 604/408 |
| 5,061,236 | 10/1991 | Sutherland et al. | 604/4 |
| 5,087,250 | 2/1992 | Lichte et al. | |
| 5,573,526 | 11/1996 | Hess | 604/408 |

FOREIGN PATENT DOCUMENTS

| | | |
|---|---|---|
| 0401016 | 5/1990 | European Pat. Off. |
| 0754468 | 7/1996 | European Pat. Off. |

*Primary Examiner*—Ronald Stright
*Assistant Examiner*—Cheryl L. Huseman
*Attorney, Agent, or Firm*—Harry G. Weissenberger

[57] ABSTRACT

A softshell reservoir has threaded fittings, one on each side of a central axis. Venous and cardiotomy blood are mixed in a mixer which screwthreadedly engages either of these fittings so the reservoir can be positioned on the right or the left of the perfusionist without crossed lines, and with a minimum of priming volume. A threaded outlet fitting may be provided on the central axis to cooperate with threaded outlet tubing to facilitate packaging and sterilizing, as well as setup and disposal.

7 Claims, 3 Drawing Sheets

BILATERALLY CONNECTABLE SOFTSHELL RESERVOIR

FIELD OF THE INVENTION

This invention relates to softshell blood reservoirs used in cardiac surgery, and more particularly to a softshell reservoir in which a single blood inlet line for cardiotomy and venous blood can be positioned on either the right or the left side of the reservoir.

BACKGROUND OF THE INVENTION

Softshell blood reservoirs are commonly used in cardiac surgery to store blood in the blood circuit of a heart-lung machine. Traditionally, the blood inlet and outlet tubing is formed integrally with the softshell reservoir. In use, the perfusionist hangs up the reservoir, unrolls the tubing, trims it as necessary, and connects it to the blood source or sources and to the pump inlet of the heart-lung machine.

Some softshell reservoirs have two inlets: one for venous blood and one for cardiotomy blood. Others have only one; these are used where venous and cardiotomy blood are already mixed upstream of the softshell reservoir. Both types of reservoirs are typically asymmetrical in design, and the blood inlets and outlet are on opposite sides of the reservoir's central vertical axis. Although the reservoir can be reversed in some instances, depending upon the mounting hardware, conventional reservoirs are typically designed for a specific position with respect to the heart-lung machine. In practice, however, the layout of the operating room may dictate a different position; i.e. the reservoir needs to be positioned sometimes on the perfusionist's right, sometimes on his left, depending upon the circumstances. This can at times be awkward by causing the inlet and outlet tubing to cross each other and interfere with sampling or other activities. It also potentially increases the length of the tubing. The latter is clinically meaningful, because it is necessary for the well-being of the patient to keep the saline priming volume of the blood circuit (of which the tubing is a part) at an absolute minimum.

SUMMARY OF THE INVENTION

The present invention provides a softshell reservoir that is usable on either the right or the left side of a heart-lung machine without crossing or lengthening lines. It achieves this result by mixing venous and cardiotomy blood in a mixer which can be connected to either of two inlet connectors that are located, respectively, on the right and left side of the reservoir. The mixer has a screwthreaded outlet and is adapted to engage screwthreaded inlet fittings formed on the softshell reservoir. This allows the blood inlet to be positioned on either side of the reservoir as desired. A centrally positioned blood outlet may be either a screwthreaded fitting or permanently connected tubing.

BRIEF DESCRIPTION OF THE DRAWINGS

FIG. 4b is a detail elevation of a blood outlet connector for use with the reservoir of FIG. 4a.

DESCRIPTION OF THE PREFERRED EMBODIMENTS

Figure 1:
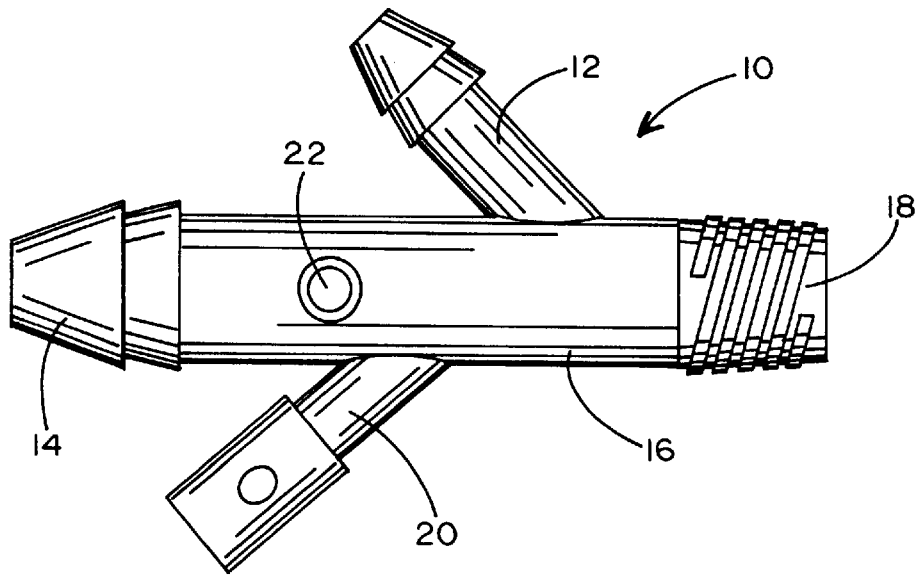
FIG. 1 is a side view of the mixer.
Figure 2:
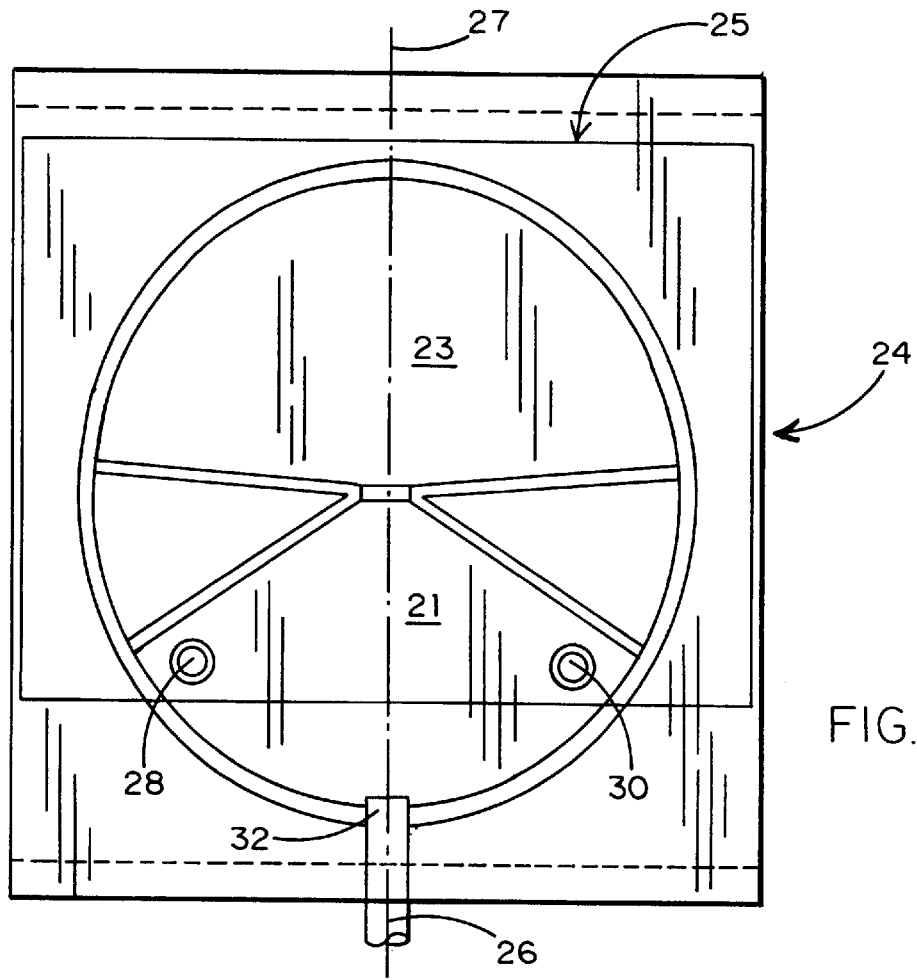
FIG. 2 is a front elevation of the softshell reservoir.

FIG. 1 illustrates the mixing of venous and cardiotomy blood prior to its introduction into the softshell reservoir of FIGS. 2 or 4, in accordance with the invention. A hollow mixer 10 has a conventional barbed connector 12 for receiving a 9.5 mm cardiotomy line coming from a source of filtered cardiotomy blood (not shown), and a barbed connector 14 for receiving a 12.7 mm venous line coming from a source of venous blood (not shown). The venous and cardiotomy blood streams mix in the body 16 of the mixer 10 and exit through the threaded end 18 of the mixer 10. A temperature probe may be inserted into the venous bloodstream at 20, and luer ports 22 may be provided in the body 16 for various purposes not material to this invention.

FIG. 2 shows a first embodiment of the softshell reservoir 24 of this invention. The reservoir 24 is may preferably be of the axisymmetrical construction described in copending application Ser. No. 08/939,383 filed on even date herewith and entitled "Two-chambered Softshell Reservoir", and may include a main chamber 21, a storage chamber 23, and a bubble trap screen 25. However, instead of the conventional three molded-in tubes for connection, respectively, to the venous source, the cardiotomy source, and the heart-lung machine (not shown), the reservoir 24 of FIG. 2 has a single molded-in outlet tube 26 for connection to the heart-lung machine, and a pair of screwthreaded inlet fittings 28, 30, one positioned on each side of the reservoir 24 and preferably equidistant from the central vertical axis 27 of the reservoir 24.

Figure 3A:
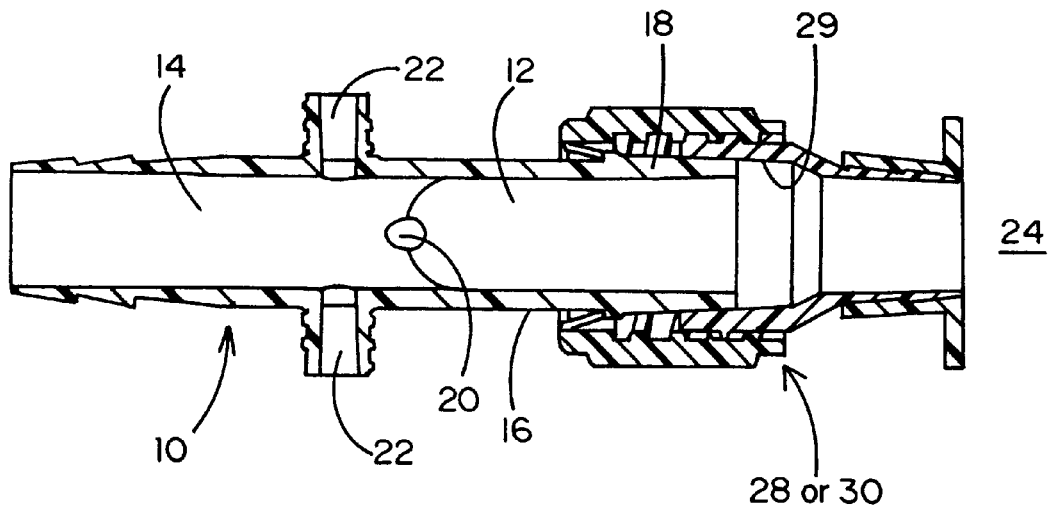
FIG. 3a is a detail vertical section of an inlet fitting with the mixer attached.

As best shown in FIG. 3a, the fittings 28 and 30 are interiorly threaded to receive the threaded end 18 of the mixer 10. The end 18 of the mixer 10 and the internal surface 29 of the fittings 28 and 30 are slightly tapered toward the reservoir 24, so that the connection between the mixer 10 and the fitting 28 or 30 will become tighter and tighter as these parts are screwed together. This assures a good seal between the mixer 10 and the reservoir 24.

Figure 3B:
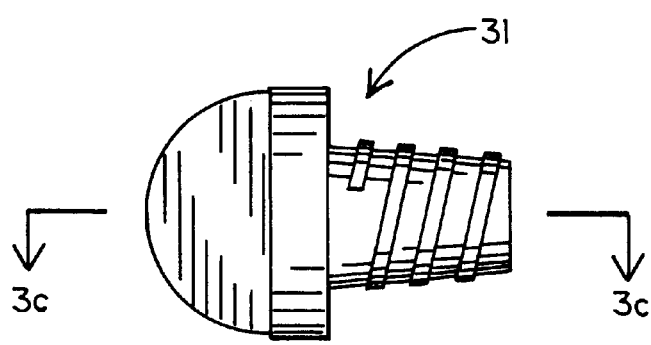
FIG. 3b is a detail side elevation of a plug for an unused fitting.
Figure 3C:
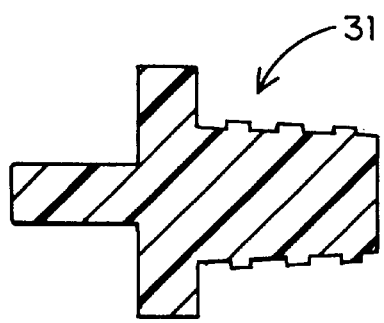
FIG. 3c is a section along line 3c—3c of FIG. 3b.

When the mixer 10 is used on one of the fittings 28, 30, the other fitting would normally be plugged by an appropriate screwthreaded plug 31 (FIGS. 3b and 3c). It should be understood, however, that the inventive softshell reservoir allows the perfusionist, if he so wishes, not to use the mixer 10 but to connect the cardiotomy line via a screwthreaded connector such as 33 (FIG. 4b) to either one of the fittings 28, 30 and the venous line to the other, as best suits a given operating room layout.

Figure 4A:
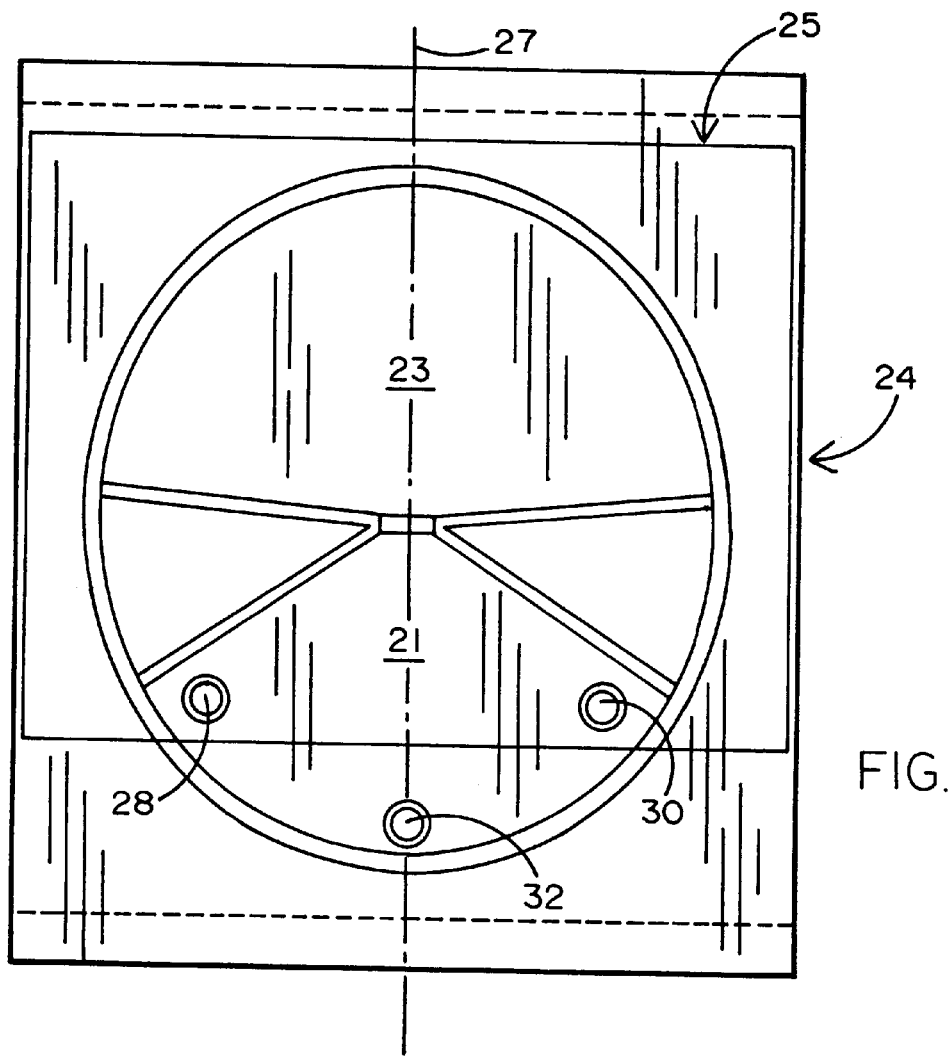
FIG. 4a is a front elevation of an alternative embodiment of the softshell reservoir.
Figure 4B:
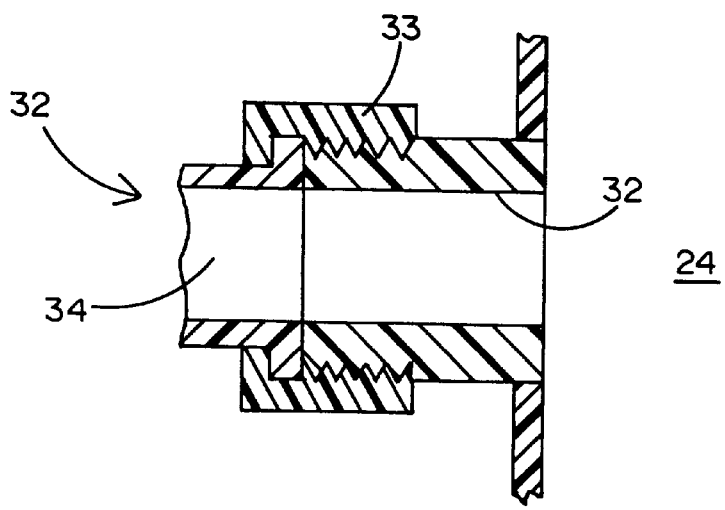

FIG. 4a illustrates a preferred embodiment of the reservoir 24. In that embodiment, the blood outlet 32 is also in the form of a screwthreaded fitting. The outlet fitting 32 receives a screwthreaded connector 33 for a tubing 34 (FIG. 4b) whose other end (not shown) is suitable for connection to a heart-lung machine. The advantage of this construction is that all the tubing associated with a softshell reservoir can be packaged and sterilized separately from the reservoir, and that it provides freedom to the perfusionist to set up the reservoir in any desired configuration. It also facilitates disposal of the equipment after surgery.

It is understood that the exemplary bilaterally connectable softshell reservoirs described herein and shown in the drawings represent only presently preferred embodiments of the invention. Indeed, various modifications and additions may be made to such embodiments without departing from the spirit and scope of the invention. Thus, other modifications and additions may be obvious to those skilled in the art and may be implemented to adapt the present invention for use in a variety of different applications.

I claim:

1. A softshell reservoir for cardiac surgery, comprising:
   a) a blood-receiving chamber which is symmetrical about a central vertical axis, and which has blood transfer ports in a wall thereof; and
   b) a pair of substantially identical fittings on said blood transfer ports, one of said fittings being positioned on one side of said central axis and the other fitting being located on the other side of said central axis, each of said fittings being arranged to releasably sealingly connect said chamber to a source of blood.

2. The reservoir of claim 1, in which said source of blood is a mixer arranged to receive venous blood and cardiotomy blood and convey a mixture thereof to said reservoir, said mixer having a blood output conduit sealingly engageable with either of said fittings.

3. The reservoir of claim 2, in which said conduit and fitting are screwthreadedly engageable with each other.

4. The reservoir of claim 3, in which said conduit and fitting are tapered so as to increase the sealing tightness of the engagement as said conduit and fitting are screwed into one another.

5. The reservoir of claim 1, further comprising a blood outlet positioned substantially on said central axis, said fittings positioned on opposite sides of said central axis being blood inlet fittings, and said blood outlet also having a fitting releasably sealably engageable with blood outlet tubing.

6. The reservoir of claim 5, in which said blood outlet fitting and said tubing are screwthreadedly engageable.

7. The reservoir of claim 6, further comprising a mixer arranged to receive venous blood and cardiotomy blood and convey a mixture thereof to said reservoir, said mixer being connected to one of said fittings positioned on opposite sides of said central axis, and the other of said fittings being plugged.

* * * * *